US012220147B2

(12) United States Patent
Shiraishi et al.

(10) Patent No.: US 12,220,147 B2
(45) Date of Patent: *Feb. 11, 2025

(54) MEDICAL DEVICE HAVING ROTATING SHAFT WITH LUMEN AND SEALING STRUCTURE

(71) Applicant: TERUMO KABUSHIKI KAISHA, Tokyo (JP)

(72) Inventors: Mizuho Shiraishi, Sagamihara (JP); Yuichi Tada, Tokyo (JP); Akihiro Takahashi, Matsuda (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 18/541,438

(22) Filed: Dec. 15, 2023

(65) Prior Publication Data
US 2024/0108379 A1     Apr. 4, 2024

Related U.S. Application Data

(63) Continuation of application No. 17/023,553, filed on Sep. 17, 2020, now Pat. No. 11,877,768, which is a
(Continued)

(30) Foreign Application Priority Data

Mar. 29, 2018 (JP) .................................. 2018-064011

(51) Int. Cl.
*A61B 17/22* (2006.01)
*A61B 17/32* (2006.01)
(Continued)

(52) U.S. Cl.
CPC ................ *A61B 17/320758* (2013.01); *A61B 17/32002* (2013.01); *A61B 2017/22078* (2013.01);
(Continued)

(58) Field of Classification Search
CPC ......... A61B 2017/22078; A61B 2017/320032; A61B 17/320758; A61B 2017/320775;
(Continued)

(56) References Cited

U.S. PATENT DOCUMENTS 4,517,977 A  5/1985 Frost
5,024,234 A  6/1991 Leary et al.
(Continued)

FOREIGN PATENT DOCUMENTS

| JP | H0194840 A | 4/1989 |
| JP | 2001517474 A | 10/2001 |
| JP | 2016221081 A | 12/2016 |

OTHER PUBLICATIONS

International Search Report (PCT/ISA/210) issued on Jun. 25, 2019, by the Japanese Patent Office as the International Searching Authority for International Application No. PCT/JP2019/012689.
(Continued)

*Primary Examiner* — Brooke Labranche
*Assistant Examiner* — Mitchell Brian Hoag
(74) *Attorney, Agent, or Firm* — BUCHANAN INGERSOLL & ROONEY PC

(57) ABSTRACT

Provided is a medical device capable of easily changing a position of the device inside a biological lumen and effectively removing a cut object. The medical device for removing the object in the biological lumen has a drive shaft, a cutting portion, a first housing that accommodates the drive shaft to be rotatable, a second housing that is rotatable with respect to the first housing, and a support portion that supports the first housing and the second housing. The second housing and the support portion relatively move along an axis to restrict relative rotation of the first housing and the second housing. The support portion supports the second housing to be rotatable around the axis.

5 Claims, 9 Drawing Sheets

Related U.S. Application Data continuation of application No. PCT/JP2019/012689, filed on Mar. 26, 2019.

(51) Int. Cl.
*A61B 17/3207* (2006.01)
*A61B 90/00* (2016.01)

(52) U.S. Cl.
CPC ............ *A61B 2017/320032* (2013.01); *A61B 2017/320775* (2013.01); *A61B 90/02* (2016.02); *A61B 2090/034* (2016.02); *A61B 2090/035* (2016.02); *A61B 2217/005* (2013.01)

(58) Field of Classification Search
CPC ............ A61B 17/32002; A61B 17/22; A61B 2217/007; A61B 2217/005; A61B 2090/035; A61B 2090/034
USPC ................ 604/22, 95.01; 606/180, 170, 159
See application file for complete search history.

(56) References Cited

U.S. PATENT DOCUMENTS

| | | | |
|---|---|---|---|
| 5,049,130 A | 9/1991 | Powell | |
| 5,062,648 A | 11/1991 | Gomringer | |
| 5,833,246 A | 11/1998 | Trott | |
| 5,921,956 A | 7/1999 | Grinberg et al. | |
| 6,129,734 A | 10/2000 | Shturman et al. | |
| 6,129,743 A | 10/2000 | Hsia et al. | |
| 6,152,941 A | 11/2000 | Himes et al. | |
| 8,657,821 B2 | 2/2014 | Palermo | |
| 9,532,783 B2 | 1/2017 | Swayze et al. | |
| 11,877,768 B2* | 1/2024 | Shiraishi | A61B 17/320758 |
| 2001/0039427 A1* | 11/2001 | Dinger | A61B 17/1659 606/167 |
| 2001/0039428 A1 | 11/2001 | Dinger et al. | |
| 2002/0058958 A1 | 5/2002 | Walen | |
| 2002/0065525 A1 | 5/2002 | Perry et al. | |
| 2005/0125009 A1* | 6/2005 | Perry | A61B 17/2909 606/139 |
| 2006/0259055 A1 | 11/2006 | Thorne et al. | |
| 2010/0102517 A1 | 4/2010 | Kumar et al. | |
| 2011/0087254 A1 | 4/2011 | Welty | |
| 2013/0060272 A1* | 3/2013 | Thistle | A61B 17/32002 606/170 |
| 2014/0100558 A1* | 4/2014 | Schmitz | A61B 17/285 606/174 |
| 2014/0277046 A1 | 9/2014 | Mark et al. | |
| 2014/0316447 A1* | 10/2014 | Ellering | A61B 17/320758 606/159 |
| 2015/0164541 A1* | 6/2015 | Shiber | A61B 17/320758 604/35 |
| 2015/0190159 A1 | 7/2015 | Mark et al. | |
| 2016/0354108 A1 | 12/2016 | Nakano et al. | |
| 2017/0340401 A1 | 11/2017 | Miller et al. | |
| 2019/0247068 A1* | 8/2019 | Whipple | A61B 17/3205 |
| 2021/0000496 A1* | 1/2021 | Herrin | A61B 17/320758 |
| 2021/0000498 A1 | 1/2021 | Shiraishi et al. | |
| 2023/0277211 A1* | 9/2023 | Tada | A61B 17/320758 606/159 |

OTHER PUBLICATIONS

An English Translation of the International Search Report (PCT/ISA/210) and the Written Opinion of the International Searching Authority (Form PCT/ISA/237) issued on Jun. 25, 2019, by the Japanese Patent Office in corresponding International Application No. PCT/JP2019/012689. (5 pages).

Office Action (Notice of Reasons for Refusal) issued Nov. 13, 2023, by the Japan Patent Office in corresponding Japanese Patent Application No. 2023-015402 and an English translation of the Office Action. (8 pages).

Office Action (The First Office Action) issued Mar. 16, 2023, by the National Intellectual Property Administration, P. R. China in corresponding Chinese Patent Application No. 201980013198.8 and an English translation of the Office Action. (16 pages).

* cited by examiner

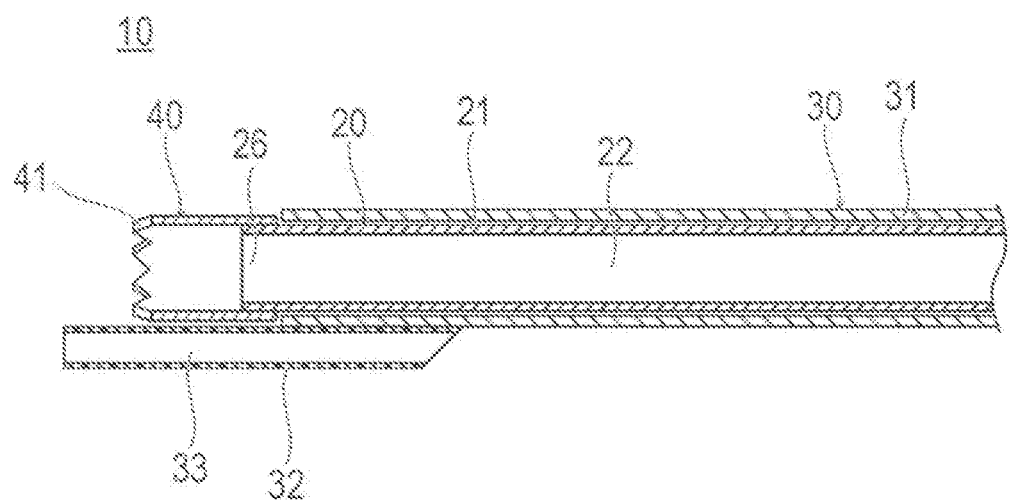
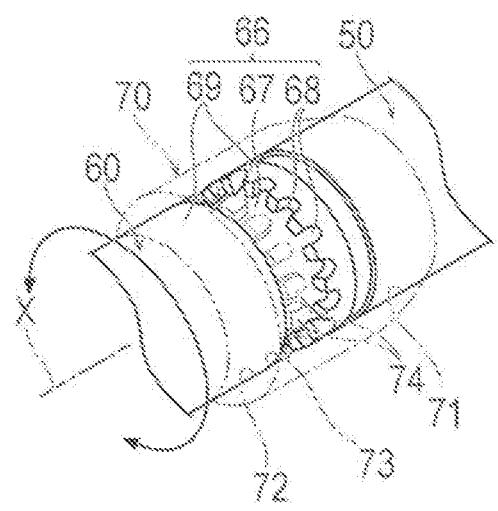 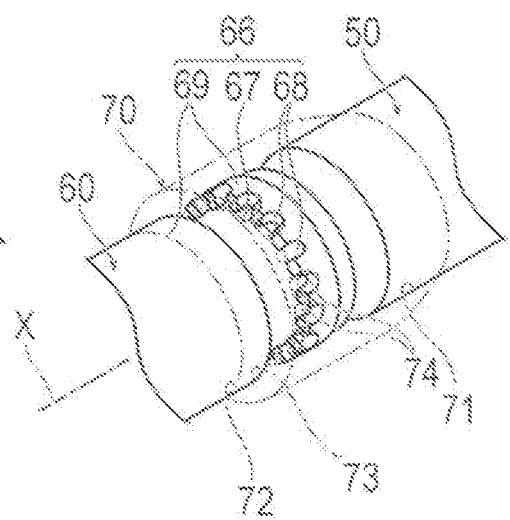

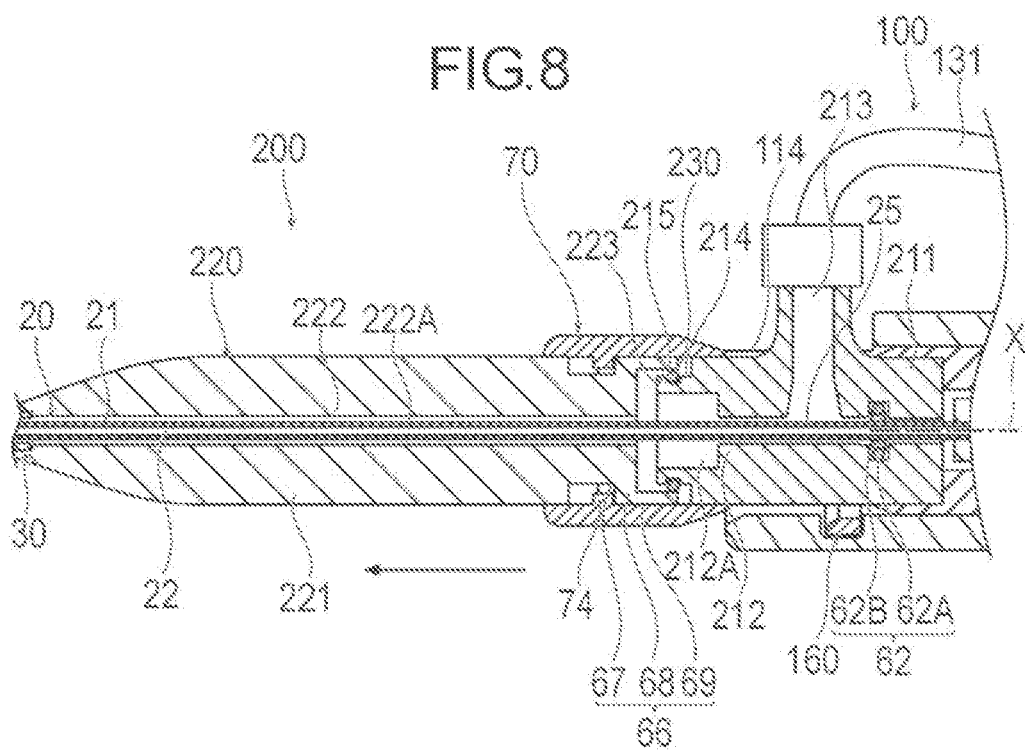

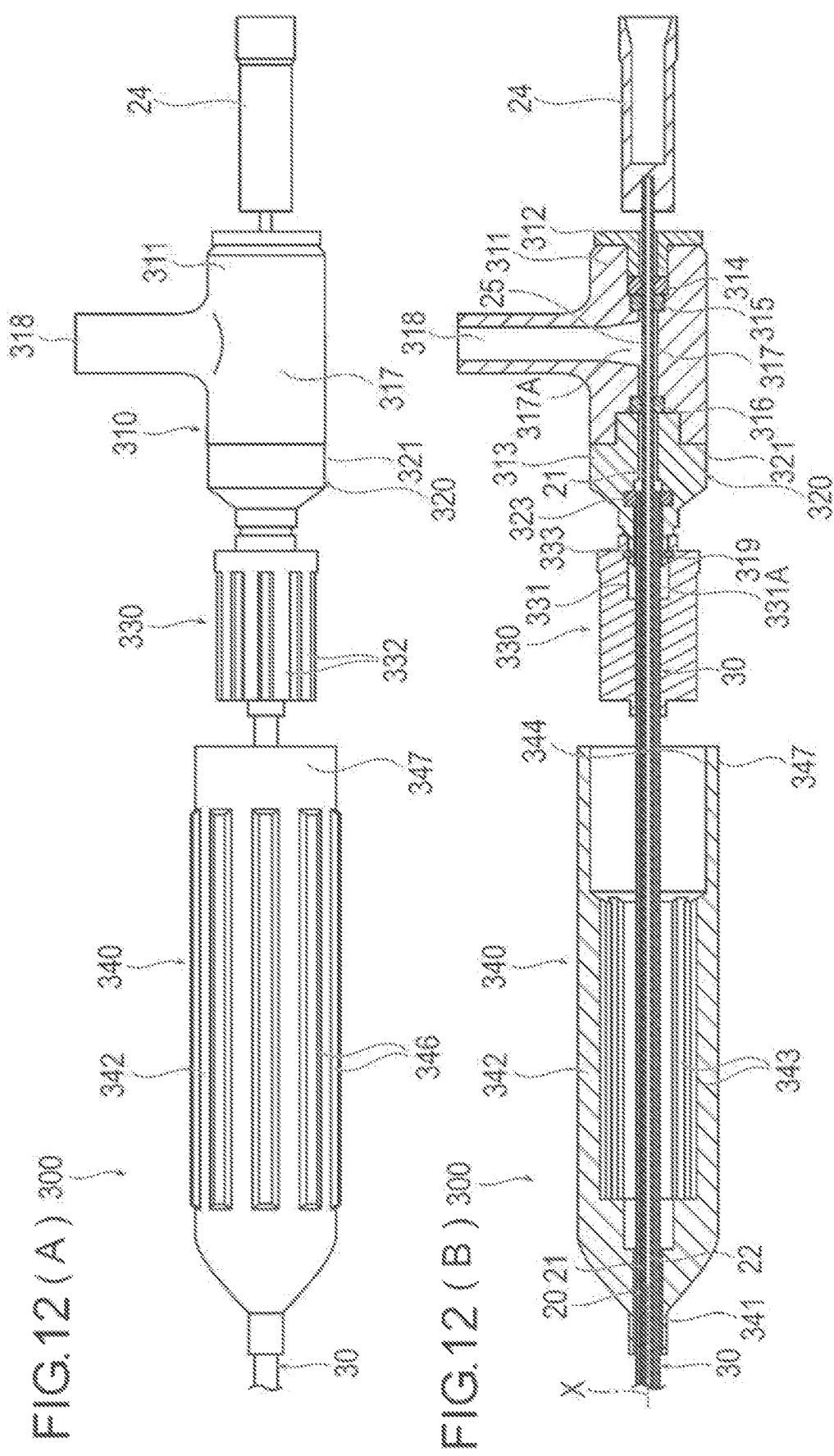

MEDICAL DEVICE HAVING ROTATING SHAFT WITH LUMEN AND SEALING STRUCTURE

CROSS-REFERENCES TO RELATED APPLICATIONS

This application is a continuation of U.S. patent application Ser. No. 17/023,553, filed on Sep. 17, 2020, which is a continuation of International Application No. PCT/JP2019/012689 filed on Mar. 26, 2019, which claims priority to Japanese Patent Application No. 2018-064011 filed on Mar. 29, 2018, the entire content of each of which is incorporated herein by reference.

FIELD OF THE INVENTION

The present invention generally relates to a medical device for removing an object in a biological lumen.

BACKGROUND DISCUSSION

Methods for treating a stenosed site caused by a plaque or a thrombus in a blood vessel include, for example, widening the blood vessel with a balloon, and causing a mesh-shaped or coil-shaped stent to indwell the blood vessel as a support for the blood vessel. However, it can be difficult to treat a stenosed site that has hardened by calcification or that appears in a bifurcated portion of the blood vessel with such methods. A known method for use in such cases involves cutting and removing the plaque, thrombus, or otherwise stenosed object.

For example, in U.S. Pat. No. 8,475,484, a device is disclosed in which an operation head for cutting an object is fixed to a distal portion of a drive shaft. The device rotates the drive shaft, thereby enabling the operation head to cut the object. An operator's hand side of the device has a sealing structure for internally sealing the device. The sealing structure includes an injection port for injecting a sealing fluid and an aspiration port for aspirating the fluid.

In a case where an orientation of the operation head of the device disclosed in U.S. Pat. No. 8,475,484 needs to be changed, it is necessary to perform an operation for changing a position of the sealing structure including the injection port and the aspiration port. However, problems in operation of the sealing structure can then arise since a tube is connected thereto. Furthermore, in the design of the device, when the position of the sealing structure is changed, a relative inclination of portions of the device in a direction intersecting with an axis of the device occurs, which can cause further problems in operation of the device.

SUMMARY

The medical device disclosed here can easily change a position of the device inside a biological lumen, and can cut and remove an object inside the biological lumen.

A medical device according to embodiments disclosed here includes a rotatable drive shaft, a cutting portion fixed to a distal portion of the drive shaft to cut the object, a first housing that accommodates the drive shaft to be rotatable, a second housing located on a distal side of the first housing and rotatable with respect to the first housing around an axis of the drive shaft, and a support portion that supports the first housing and the second housing. Any one of two among the first housing, the second housing, and the support portion has a recess portion, and the other one has a projection portion fittable into and detachable from the recess portion by relatively moving along the axis. The projection portion and the recess portion are fitted together to restrict relative rotation of the first housing and the second housing. The support portion supports at least one of the first housing and the second housing to be rotatable around the axis. The support portion restricts a relative inclination of the first housing and the second housing in a direction intersecting with the axis.

More generally, a medical device includes a rotatable drive shaft, a cutting portion fixed to a distal portion of the drive shaft to cut the object, a first housing that accommodates the drive shaft to be rotatable, a second housing located on a distal side of the first housing and rotatable with respect to the first housing around an axis of the drive shaft, and a support portion that supports the first housing and the second housing. The relative rotation of the first housing and the second housing is restricted. The support portion supports the first housing to be rotatable around the axis. The support portion restricts a relative inclination of the first housing and the second housing in a direction intersecting with the axis.

In the medical device configured as described above, the second housing is rotatable with respect to the first housing. Accordingly, a position of the medical device inside the biological lumen can be easily changed by operating the second housing. In addition, even if the first housing and the second housing are supported by the support portion and are relatively rotated, the drive shaft is rotatable at a proper position. Therefore, the medical device can effectively cut and remove the object in the biological lumen by using the cutting portion fixed to the drive shaft. The projection portion and the recess portion may be disposed in the first housing, the second housing, the support portion interlocked with the first housing, or the support portion interlocked with the second housing.

According to another aspect of the medical device configured as described above, the second housing is rotatable with respect to the first housing. Accordingly, a position of the medical device inside the biological lumen can be easily changed by operating the second housing. In addition, even if the first housing and the second housing are supported by the support portion and are relatively rotated, the drive shaft is rotatable at a proper position. Therefore, the medical device can effectively cut and remove the object in the biological lumen by using the cutting portion fixed to the drive shaft. The relative rotation of the first housing and the second housing is restricted. Accordingly, the first housing and the second housing can be easily aligned at any desired positions in a circumferential direction.

A method associated with the present disclosure involves inserting a medical device into the biological lumen, rotating a first portion of the medical device relative to a second portion of the medical device to change a position of a cutting portion of the medical device relative to the object, the first portion of the medical device supporting a tube, locking relative rotation between the first portion of the medical device and the second portion of the medical device, rotating a drive shaft supported by the second portion of the medical device, the drive shaft being disposed within the tube, to rotate the cutting portion to cut the object, and aspirating the object from the biological lumen through the drive shaft.

BRIEF DESCRIPTION OF THE DRAWINGS

FIG. 3 is a sectional view illustrating a distal portion of the medical device.

FIGS. 4A and 4B are enlarged perspective views illustrating a support portion of the medical device when transparently viewed through a dashed-dotted line. FIG. 4A illustrates a state before a projection portion is fitted into a recess portion, and FIG. 4B illustrates a state where the projection portion is fitted into the recess portion.

FIG. 5A illustrates a state where the medical device engages with the drive device, and FIG. 5B illustrates a state where the medical device is detachable from the drive device.

FIG. 8 is a sectional view illustrating a state where the projection portion is fitted into the recess portion in the medical device according to the second embodiment.

FIG. 9A is a plan view, and FIG. 9B is a sectional view.

FIGS. 12A and 12B are views illustrating a modification example of the medical device according to the third embodiment. FIG. 12A is a plan view, and FIG. 12B is a sectional view.

DETAILED DESCRIPTION

Figure 1:
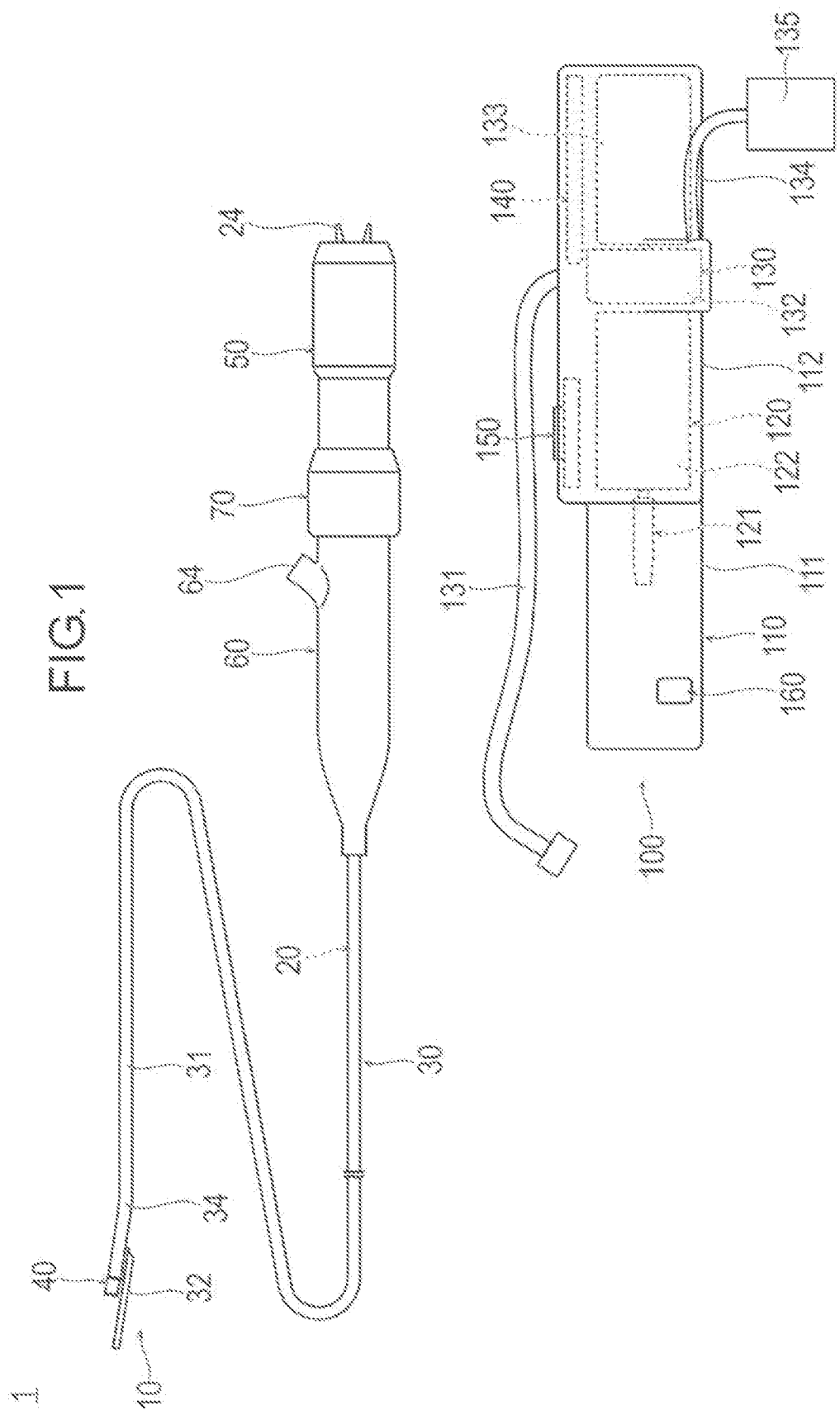
FIG. 1 is a plan view illustrating a medical device and a drive device according to a first embodiment.

Set forth below with reference to the accompanying drawings is a detailed description of embodiments of a medical device and method for removing an object in a biological lumen representing examples of the inventive medical device and method. In some cases, a size or a ratio of each member in the drawings may be exaggerated for convenience of description, and may be different from an actual size or an actual ratio.

First Embodiment

A medical device 10 according to a first embodiment is inserted into a blood vessel in an acute lower limb ischemia or a deep vein thrombosis, and is used for a treatment to destroy and remove a thrombus, a plaque, an atheroma, or a calcified lesion. In the present specification, a side of the device which is inserted into the blood vessel will be referred to as a "distal side", and an operator's hand side will be referred to as a "proximal side". Without being necessarily limited to a thrombus, plaque, atheroma, or calcified lesion, an object to be removed is applicable to any object that may be present inside a biological lumen.

Figure 2:
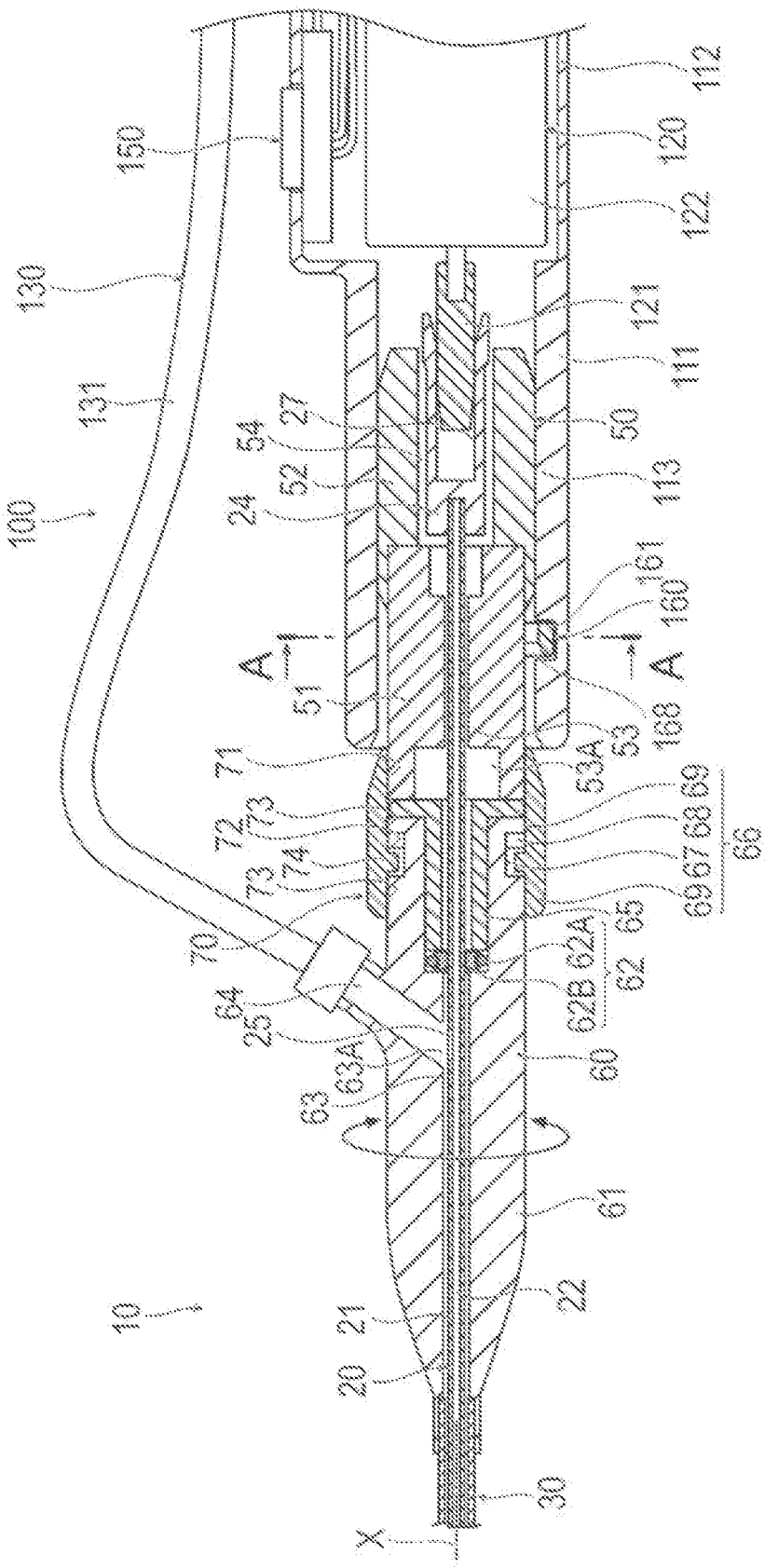
FIG. 2 is a sectional view illustrating a proximal portion of the medical device according to the first embodiment.

As illustrated in FIGS. 1 to 3, the medical device 10 is interlocked with and driven by a drive device 100 that generates a drive force. The medical device 10 and the drive device 100 configure one medical system 1.

The medical device 10 includes an elongated drive shaft 20 that is rotationally driven, an outer tube 30 that accommodates the drive shaft 20, and a cutting portion 40 that cuts a thrombus. The medical device 10 further includes a first housing 50 that holds a proximal portion of the drive shaft 20 to be rotatable, a second housing 60 that is fixed to a proximal portion of the outer tube 30, and a support portion 70.

The drive shaft 20 transmits a rotational force to the cutting portion 40. The drive shaft 20 has an aspiration lumen 22 (lumen) for transporting a cut object to a proximal side. The drive shaft 20 includes an elongated tubular drive tube 21 having an axis X, and a connection section 24 fixed to a proximal portion of the drive tube 21.

The drive tube 21 penetrates the outer tube 30, and the cutting portion 40 is fixed to a distal portion of the drive tube 21. The proximal portion of the drive tube 21 is located inside the second housing 60. The drive tube 21 is rotationally driven by a rotary drive shaft 121 (to be described later) via the connection section 24. A distal end of the drive tube 21 has an inlet portion 26 which an aspiration target (cut thrombus) enters. A proximal end of the drive tube 21 has a closed lumen, and is fixed to the connection section 24. In the drive tube 21, a side surface of the proximal portion located inside the second housing 60 has an outlet portion 25 in which the aspiration lumen 22 is open. The outlet portion 25 is an exit through which a thrombus entering the inside of the drive tube 21 from the inlet portion 26 is discharged.

The drive tube 21 is flexible, and has a characteristic in which rotational power acting from a proximal side can be transmitted to a distal side. A surface of the proximal portion of the drive tube 21 located inside the first housing 50 and the second housing 60 has a smooth surface property, and has high dimensional accuracy. In this manner, the drive tube 21 is rotatable at high speed inside the first housing 50 and the second housing 60 while being sealed with a first seal portion 62 (to be described later). The surface of the drive tube 21 may be subjected to plating treatment or polishing treatment in order to have the smooth surface property.

As a whole, the drive tube 21 may be configured to include one member, or may be configured to include a plurality of members. For example, the distal portion and the proximal portion of the drive tube 21 may be configured to include different members. For example, a portion of the drive tube 21 may be a tubular body in which a plurality of wire rods are aligned and interlocked with each other in a spiral shape. Alternatively, the drive tube 21 may have spiral slits or grooves formed by laser processing in order to adjust rigidity depending on a portion of the drive tube 21.

For example, as a configuration material of the drive tube 21, it is possible to preferably use stainless steel, Ta, Ti, Pt, Au, W, polyolefin such as polyethylene and polypropylene, polyester such as polyamide and polyethylene terephthalate, and fluorine-based polymer such as ETFE, polyether ether ketone (PEEK), and polyimide. In addition, the drive tube 21 may be formed of a plurality of materials, and an incorporated reinforcement member such as a wire rod.

The connection section 24 is a substantially columnar member fixed to the proximal end of the drive tube 21. The connection section 24 is a member that is interlocked with the rotary drive shaft 121 and receives rotational power. A proximal portion of the connection section 24 includes a fitting recess portion 27 into which the rotary drive shaft 121 is fitted. The connection section 24 seals a lumen of the proximal end of the drive tube 21.

The outer tube 30 includes an outer tube main body 31 that accommodates the drive shaft 20 to be rotatable, and a distal tube 32 that is fixed to a side surface of a distal portion of the outer tube main body 31.

The outer tube main body 31 is a tubular body, and a proximal end is fixed to the second housing 60. A distal end of the outer tube main body 31 is located on a proximal side of the cutting portion 40. The distal portion of the outer tube main body 31 has a curved portion 34 that is curved at a predetermined angle. The curved portion 34 can be used to change an orientation of the distal end of the outer tube main body 31 by rotating the outer tube main body 31.

The distal tube 32 is fixed to an outer peripheral surface of the distal portion of the outer tube main body 31. The distal tube 32 internally has a guide wire lumen 33 into which a guide wire can be inserted.

For example, as a configuration material of the outer tube main body 31 and the distal tube 32, it is possible to preferably use polyolefin such as polyethylene and polypropylene, polyester such as polyamide and polyethylene terephthalate, various elastomers, fluorine-based polymer such as ETFE, polyether ether ketone (PEEK), or polyimide. In addition, the outer tube main body 31 may be formed of a plurality of materials, and may have an incorporated reinforcement member such as a wire rod.

The cutting portion 40 is a member for cutting a thrombus. The cutting portion 40 is fixed to an outer peripheral surface of the distal portion of the drive tube 21. The cutting portion 40 is a cylinder that projects to the distal side of the drive tube 21. A distal end of the cutting portion 40 includes a sharp blade 41. A shape of the blade 41 is not particularly limited. The cutting portion 40 may have many fine abrasive grains instead of the blade 41.

A configuration material of the cutting portion 40 preferably has strength which enables the thrombus to be cut. For example, it is possible to preferably use stainless steel, Ta, Ti, Pt, Au, W, or a shape memory alloy. The configuration material of the cutting portion 40 may be an engineering plastic resin such as polyether ether ketone (PEEK).

The first housing 50 includes a first housing main body 51 and a joint 52. The first housing main body 51 includes a first space-defining portion 53. The first space-defining portion 53 has a first internal space 53A through which the drive tube 21 rotatably penetrates. The support portion 70 is fixed to an outer peripheral surface of a distal portion of the first housing main body 51. The joint 52 is fixed to a proximal portion of the first housing main body 51. The joint 52 can be inserted into and interlocked with an interlock port 111 of the drive device 100 (to be described later). The joint 52 has a joint opening portion 54 on a proximal side, and internally accommodates the connection section 24.

The second housing 60 includes a second housing main body 61, the first seal portion 62, a fixing member 65, and an engagement portion 66 which engages with the support portion 70. The second housing main body 61 includes a second space-defining portion 63 and an aspiration port 64. The second space-defining portion 63 has a second internal space 63A through which the drive tube 21 rotatably penetrates. An aspiration tube 131 of the drive device 100 (to be described later) can be connected to the aspiration port 64. The aspiration port 64 communicates with the second internal space 63A. A proximal end of the outer tube 30 is fixed to a distal portion of the second housing main body 61 in a liquid-tight manner. The proximal portion of the drive tube 21 penetrating the outer tube 30 is located in the second internal space 63A. The outlet portion 25 of the drive tube 21 is located in the second internal space 63A. Therefore, negative pressure acting on the aspiration port 64 from the aspiration tube 131 acts on the inside of the drive tube 21 from the outlet portion 25. The first seal portion 62 which comes into contact with an outer peripheral surface of the drive tube 21 is disposed on a proximal side of the second space-defining portion 63. The first seal portion 62 prevents negative pressure in the second internal space 63A from being released. The first seal portion 62 includes a ring-shaped outer seal portion 62A and a ring-shaped inner seal portion 62B disposed inside the outer seal portion 62A.

The outer seal portion 62A has high dimensional accuracy, a smooth surface property, and high flexibility (adhesion). In this manner, the outer seal portion 62A comes into close contact with a contact target with high dimensional accuracy without any gap, and is excellent in sealing performance. An outer peripheral surface of the outer seal portion 62A comes into contact with an inner peripheral surface of the second space-defining portion 63. An inner peripheral surface of the outer seal portion 62A comes into contact with an outer peripheral surface of the inner seal portion 62B. For example, the outer seal portion 62A is an O-ring. For example, a configuration material of the outer seal portion 62A includes natural rubber, synthetic rubber, and silicone resin.

The inner seal portion 62B has a small dimension, high dimensional accuracy, and a smooth surface property. The inner seal portion 62B has sealing performance lower than that of the outer seal portion 62A, but is excellent in slidability. The outer peripheral surface of the inner seal portion 62B comes into contact with the inner peripheral surface of the outer seal portion 62A. An inner peripheral surface of the inner seal portion 62B comes into contact with the outer peripheral surface of the drive tube 21 that rotates at a high speed. The inner seal portion 62B is excellent in the slidability. Accordingly, while sliding with the drive tube 21, the inner seal portion 62B prevents the negative pressure in the second internal space 63A from being released.

The inner seal portion 62B comes into contact with the drive tube 21 that rotates at a high speed. Accordingly, it is preferable that the inner seal portion 62B has low frictional resistance, high heat resistance, a low linear expansion coefficient, and high wear resistance. For example, a configuration material of the inner seal portion 62B includes a fluorine-based resin such as ultrahigh molecular weight polyethylene, polyester, polyamide, and polytetrafluoroethylene, or a combination of two or more materials described above (polymer alloy, polymer blend, and laminate).

The fixing member 65 is a tubular member that fixes a seal portion to the second housing main body 61. The fixing member 65 enters the second internal space 63A from a proximal side of the second housing main body 61, and is in contact with a proximal side surface of the first seal portion 62.

As illustrated in FIGS. 2, 4A, and 4B, the engagement portion 66 is disposed on an outer peripheral surface of a proximal portion of the second housing main body 61. The engagement portion 66 includes a sliding surface 69 that is a perfect circle having a smooth cross-sectional shape, a groove portion 67 that extends in a circumferential direction, and a plurality of recess portions 68 that are aligned in a proximal side edge of the groove portion 67 in the circumferential direction. The number of recess portions 68 is not particularly limited. The sliding surface 69 is disposed on both a distal side and a proximal side of the groove portion 67. The sliding surface 69 may be disposed on only one of the distal side and the proximal side of the groove portion 67.

The support portion 70 is a tubular member that guides and limits a relative movement of the first housing 50 and the second housing 60. A proximal inner peripheral surface 71 located in a proximal portion of the support portion 70 is fixed to an outer peripheral surface on a distal side of the first housing 50. A distal inner peripheral surface 72 located in a distal portion of the support portion 70 has a support sliding surface 73 which is a perfect circle having a smooth cross-sectional shape, and a plurality of projection portions 74 aligned in the circumferential direction. An inner diameter of the support sliding surface 73 is slightly larger than an outer diameter of the facing sliding surface 69. The support sliding surface 73 comes into close contact with the sliding surface 69 to be slidable with respect to the sliding surface 69. The projection portion 74 has a shape projecting to a proximal side while projecting inward in a radial direction from the support sliding surface 73. The projection portion 74 is accommodated in the groove portion 67 of the second housing 60, and is movable inside the groove portion 67. It is preferable that the number of the projection portions 74 and the number of the recess portions 68 coincide with each other. However, the numbers may not coincide with each other. A length of the projection portion 74 in the direction along the axis X is shorter than a length of the groove portion 67 in the direction along the axis X. The projection portion 74 has a shape that can be fitted into the recess portion 68 toward a proximal side and can be detached from the recess portion 68 toward a distal side. The projection portion 74 is movable in the circumferential direction with respect to the groove portion 67 in a state of being accommodated in the groove portion 67. The support portion 70 restricts the relative movement of the first housing 50 and the second housing 60 in a direction intersecting with the axis X. In addition, the support portion 70 restricts a relative inclination of the first housing 50 and the second housing 60.

Next, the drive device 100 will be described.

As illustrated in FIGS. 1 and 2, the drive device 100 includes a casing 110, a drive unit 120 that generates a rotational force, an aspiration portion 130 that generates an aspiration force, a battery 140, and a switch 150.

The drive unit 120 includes the rotary drive shaft 121 and a first motor 122. The rotary drive shaft 121 can be connected to the connection section 24 of the medical device 10. The first motor 122 obtains electric power from the battery 140, and rotates the rotary drive shaft 121. A rotation speed of the first motor 122 is not particularly limited. For example, the rotation speed is 5,000 to 200,000 rpm.

The aspiration portion 130 includes the aspiration tube 131, a pump 132, a second motor 133, a waste liquid tube 134, and a waste liquid pack 135. The aspiration tube 131 can be connected to the aspiration port 64 of the medical device 10. The second motor 133 obtains electric power from the battery 140, and drives the pump 132. The pump 132 is driven by the second motor 133 to apply the negative pressure to the aspiration tube 131. In addition, the pump 132 discharges a fluid aspirated through the aspiration tube 131 to the waste liquid tube 134. The waste liquid tube 134 is interlocked with the pump 132. The waste liquid tube 134 transport a waste liquid discharged from the pump 132 to the waste liquid pack 135.

The switch 150 is a portion operated to start and stop electric power supply from the battery 140 to the first motor 122 and the second motor 133. The switch 150 is fixed to the casing 110. Each time the switch 150 is pressed, the electric power supply is switched on and off.

The casing 110 includes the interlock port 111 disposed in a distal portion and an accommodation portion 112 disposed in a proximal portion.

The accommodation portion 112 accommodates the first motor 122, the second motor 133, the pump 132, and the battery 140. In addition, the switch 150 is fixed to the accommodation portion 112 to be operably exposed on an outer surface. The aspiration tube 131 and the waste liquid tube 134 are led out from the accommodation portion 112.

The interlock port 111 is a portion into which the joint 52 of the medical device 10 is inserted and interlocked with the joint 52. The interlock port 111 includes a receiving portion 113 which comes into in contact with an outer peripheral surface of the joint 52, and an interlock portion 160 detachably interlocked with the first housing 50.

Figure 5:
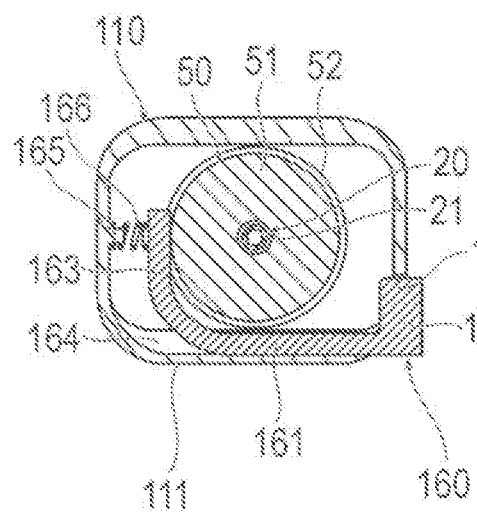
FIGS. 5A and 5B are sectional views taken along line A-A in FIG. 2.
Figure 5:
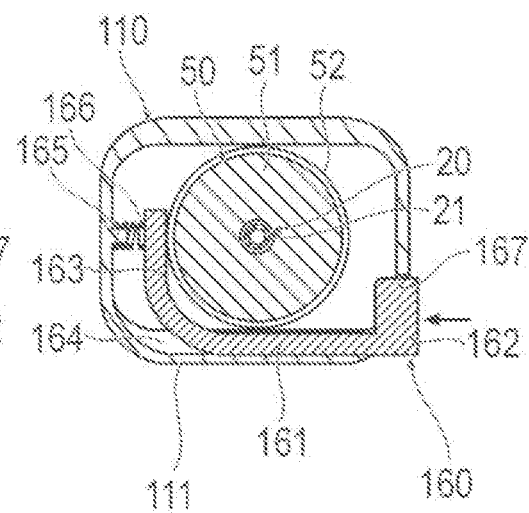

As illustrated in FIGS. 2 and 5A, the interlock portion 160 includes a pressing portion 161 subjected to a switching operation by an operator, a sliding groove 164 in which the pressing portion 161 slides, an elastic member 166 that biases the pressing portion 161, and a projection portion 165 that restricts a position of the elastic member 166. The sliding groove 164 is formed on an inner peripheral surface of the interlock port 111 in a direction orthogonal to the axis X of the drive tube 21. One end of the sliding groove 164 communicates with a through-hole 167 that penetrates from the inner peripheral surface to an outer peripheral surface of the interlock port 111. The pressing portion 161 is accommodated in the sliding groove 164 to be slidable. The pressing portion 161 includes an operation unit 162 exposed outward from the through-hole 167, and a contact portion 163 configured to contact an outer peripheral surface of the first housing main body 51. An inner edge 168 on a distal side of the contact portion 163 is inclined to be widened toward the distal side. The projection portion 165 is formed on the inner peripheral surface of the interlock port 111 on a side opposite to a side having the through-hole 167. For example, the elastic member 166 is a coil spring. One end of the elastic member 166 is fitted and fixed to the projection portion 165. The other end of the elastic member 166 is in contact with the contact portion 163. The elastic member 166 is in contact with the contact portion 163 in a further contracted state as compared with a natural state where no external force acts. Therefore, the elastic member 166 biases the contact portion 163 toward the first housing main body 51. When the contact portion 163 is contacted with the first housing main body 51 by a biasing force of the elastic member 166, the first housing main body 51 is interlocked with the interlock port 111. At this time, the contact portion 163 is located on a distal side of the joint 52. Therefore, the joint 52 cannot be separated to a distal side from the interlock port 111. When the operator presses the operation unit 162, the pressing portion 161 moves in the sliding groove 164 as illustrated in FIG. 5B. In this manner, the elastic member 166 contracts, and the contact portion 163 is separated from the outer peripheral surface of the first housing main body 51. Therefore, the first housing main body 51 is released from a biasing force of the elastic member 166. In addition, the contact portion 163 moves to a position deviated from a distal side position of the joint 52. In this manner, the first housing 50 can be detached to the distal side from the interlock port 111 without being hindered by the contact portion 163.

Next, a method of using the medical device 10 according to the first embodiment will be described as an example by adopting a case of destroying and aspirating a thrombus or a calcified lesion inside a blood vessel.

First, the operator inserts a guide wire (not illustrated) into a blood vessel so that the guide wire reaches the vicinity of the thrombus. Next, the operator inserts a proximal end of the guide wire into the guide wire lumen 33 of the medical device 10. Thereafter, the medical device 10 is caused to reach the vicinity of the thrombus by using the guide wire as a guide.

Next, as illustrated in FIG. 2, the operator inserts the joint 52 of the medical device 10 into the interlock port 111 of the drive device 100. In this manner, the inner edge 168 of the contact portion 163 located in the interlock port 111 is laterally pushed by the joint 52. Therefore, the elastic member 166 contracts and laterally moves. In this manner, the joint 52 moves to a proximal side inside the interlock port 111 by passing across the contact portion 163. The joint 52 comes into close contact with the receiving portion 113. When the joint 52 passes across the contact portion 163, as illustrated in FIG. 5A, the contact portion 163 is pushed by the elastic member 166, and is contacted with the first housing main body 51. In this manner, the first housing main body 51 is interlocked with the interlock port 111. At this time, the contact portion 163 is located on the distal side of the joint 52. Therefore, the joint 52 is restricted from being separated to the distal side from the interlock port 111. In addition, the rotary drive shaft 121 is connected to the connection section 24. Next, as illustrated in FIG. 2, the operator interlocks the aspiration tube 131 with the aspiration port 64.

The operator rotates the outer tube 30 in a case where a position of the cutting portion 40 needs to be changed in the circumferential direction. When the outer tube 30 is rotated, a direction of the curved portion 34 of the outer tube 30 is changed, and the position of the cutting portion 40 can be changed. When the outer tube 30 is rotated, as illustrated in FIGS. 2 and 4A, the operator moves the second housing 60 to the proximal side with respect to the drive device 100 to which the first housing 50 is fixed. In this manner, the projection portion 74 of the support portion 70 is not fitted into the recess portion 68 located in the second housing main body 61, and is brought into an accommodated state in the groove portion 67. In this state, the projection portion 74 is movable in the circumferential direction with respect to the groove portion 67. Therefore, the operator can rotate the second housing 60 with respect to the drive device 100 and the first housing 50. When the second housing 60 is rotated, the outer tube 30 fixed to the second housing 60 is rotated. In this manner, a direction of the curved portion 34 of the outer tube 30 is changed, and the position of the cutting portion 40 can be changed. Therefore, without rotating the drive device 100, which is less easily rotated, the second housing 60 is rotated. In this manner, the direction of the cutting portion 40 can be easily changed within a relatively large range.

Figure 6:
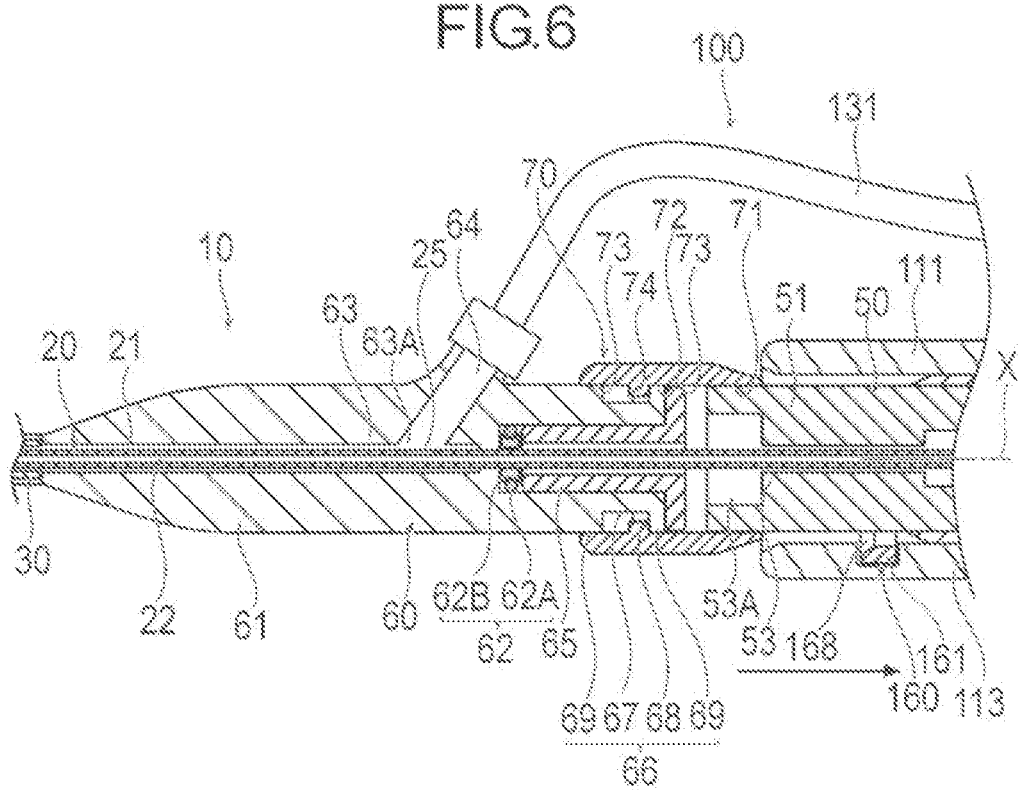
FIG. 6 is a sectional view illustrating a proximal portion of the medical device in a state where the projection portion is fitted into the recess portion.

After the operator adjusts the direction of the outer tube 30, as illustrated in FIGS. 4B and 6, the operator moves the second housing 60 to the distal side with respect to the drive device 100 to which the first housing 50 is fixed. In this manner, the projection portion 74 of the support portion 70 is fitted into the recess portion 68 located in the second housing main body 61. Therefore, the second housing 60 cannot be rotated with respect to the first housing 50 and the drive device 100. That is, the second housing 60 can be integrally operated with the first housing 50 and the drive device 100. Then, when the drive shaft 20 is rotated to cut and aspirate the thrombus, the outer tube 30 and the second housing 60 can be prevented from being rotated by following the drive shaft 20 due to a frictional force received from the drive shaft 20.

Next, the operator presses the switch 150 (refer to FIG. 1). In this manner, electric power is supplied from the battery 140 to the first motor 122 and the second motor 133. The first motor 122 rotates the rotary drive shaft 121, and rotates the connection section 24 connected to the rotary drive shaft 121. In this manner, the drive shaft 20 is rotated, and the cutting portion 40 is rotated. The rotating cutting portion 40 cuts the thrombus inside the blood vessel.

The second motor 133 operates the pump 132. In this manner, as illustrated in FIG. 6, negative pressure acts on the second internal space 63A via the aspiration tube 131. Therefore, the negative pressure acts on the aspiration lumen 22 of the drive tube 21 from the outlet portion 25 located in the second internal space 63A. Therefore, the thrombus cut by the blade 41 of the cutting portion 40 passes through the inside of the cutting portion 40, and is aspirated into the aspiration lumen 22 from the inlet portion 26 of the drive tube 21. The first seal portion 62 that seals a portion between the outer peripheral surface of the drive tube 21 and the second housing main body 61 is disposed on the proximal side of the second internal space 63A. Furthermore, the first seal portion 62 has the inner seal portion 62B which can come into contact with the drive tube 21 that rotates at a high speed. Furthermore, the first seal portion 62 has the outer seal portion 62A having high sealing performance for sealing a portion between the inner seal portion 62B and the second housing main body 61. In this manner, the first seal portion 62 can effectively seal a portion between the drive tube 21 that rotates at a high speed and the second housing main body 61. Therefore, a pressure loss is extremely small in the first seal portion 62. Therefore, the thrombus can be satisfactorily aspirated from the inlet portion 26.

The aspirated thrombus reaches the pump 132 through the outlet portion 25, the second internal space 63A, and the aspiration tube 131. As illustrated in FIG. 1, the thrombus reaching the pump 132 is discharged to the waste liquid pack 135 via the waste liquid tube 134. After the thrombus is completely cut and aspirated, the operator presses the switch 150. In this manner, the electric power supply from the battery 140 to the first motor 122 and the second motor 133 is stopped. Therefore, the rotation of the drive shaft 20 is stopped, and the pump 132 is stopped. In this manner, the cutting performed by the cutting portion 40 and the aspiration performed by the drive tube 21 are stopped. Thereafter, the medical device 10 is removed from the blood vessel, and the treatment is completed.

As described above, according to the first embodiment, there is provided the medical device 10 for removing the object inside the biological lumen. The medical device 10 includes the rotatable drive shaft 20, the cutting portion 40 fixed to a distal portion of the drive shaft 20 to cut the object, the first housing 50 that accommodates the drive shaft 20 to be rotatable, the second housing 60 located on the distal side of the first housing 50, accommodating the drive shaft 20 to be rotatable, and rotatable with respect to the first housing 50 around the axis X of the drive shaft 20, and the support portion 70 that supports the first housing 50 and the second housing 60. Any one of the second housing 60 and the support portion 70 has the recess portion 68, and the other one has the projection portion 74 fittable into and detachable from the recess portion 68 by relatively moving along the axis X. The projection portion 74 and the recess portion 68 are fitted together to restrict relative rotation of the first housing 50 and the second housing 60. The support portion 70 supports at least one of the first housing 50 and the second housing 60 to be rotatable around the axis X. The support portion 70 restricts a relative movement and a relative inclination of the first housing 50 and the second housing 60 in a direction intersecting with the axis X.

In the medical device 10 configured as described above, the second housing 60 can be rotated with respect to the first housing 50. Accordingly, the position of the medical device 10 inside the biological lumen can be easily changed by operating the second housing 60. In addition, the support portion 70 is disposed in the medical device 10. Accordingly, even when the first housing 50 and the second housing 60 are relatively rotated, the axes of the first housing 50 and the second housing 60 are not changed. Therefore, the drive shaft 20 can be rotated at a proper position, and the object in the biological lumen can be effectively cut and removed. Furthermore, the projection portion 74 is fitted into the recess portion 68. In this manner, the second housing 60 cannot be rotated with respect to the first housing 50. In this manner, the medical device 10 can integrally operate the first housing 50 and the second housing 60, thereby improving operability. In addition, the relative movement and the relative inclination of the first housing 50 and the second housing 60 in the direction intersecting with the axis X are restricted. Accordingly, a load of the drive shaft 20 can be reduced.

In addition, the medical device 10 has the outer tube 30 fixed to the second housing 60 and accommodating the drive shaft 20 to be rotatable. Therefore, the orientation of the outer tube 30 accommodating the drive shaft 20 can be changed by rotating the second housing 60. Therefore, the position of the medical device 10 inside the biological lumen can be easily changed by operating the second housing 60.

In addition, the second housing 60 has the aspiration port 64 that receives the aspiration force from the outside. At least a portion of the drive shaft 20 has a tubular shape, and the aspiration lumen 22 of the drive shaft 20 communicates with the aspiration port 64. The first seal portion 62 which comes into contact with an outer peripheral surface of the drive shaft 20 is disposed in a proximal portion of the second housing 60 where the aspiration port 64 is formed. In this manner, the support portion 70 causes the axes of the first housing 50 and the second housing 60 to coincide with each other. Accordingly, even when the first housing 50 and the second housing 60 are relatively rotated or moved, the positions of the first seal portion 62 and the drive shaft 20 are properly maintained. Therefore, the medical device 10 can reduce the pressure loss in the first seal portion 62, and can effectively apply the aspiration force to the lumen of the drive shaft 20.

In addition, the first seal portion 62 has the ring-shaped outer seal portion 62A which comes into contact with the second housing 60 and the ring-shaped inner seal portion 62B which comes into contact with the drive shaft 20. The outer seal portion 62A is more flexible than the inner seal portion 62B. The inner seal portion 62B comes into contact with the inner peripheral surface of the outer seal portion 62A, and the inner seal portion 62B has the frictional resistance smaller than that of the outer seal portion 62A. In this manner, the inner seal portion 62B slides with the drive shaft 20 with low friction, and achieves excellent sealing performance while preventing the rotation of the drive shaft 20 from being hindered. Then, the flexible outer seal portion 62A prevents the pressure loss caused by a gap between the inner seal portion 62B and the second housing 60. Therefore, the first seal portion 62 has the outer seal portion 62A and the inner seal portion 62B so that the pressure loss can be reduced without hindering the rotation of the rotating drive shaft 20.

In addition, the second housing 60 is movable with respect to the first housing 50 along the axis X of the drive shaft 20. The support portion 70 is disposed in the medical device 10. Accordingly, even when the second housing 60 moves along the axis X with respect to the first housing 50, the axes of the second housing 60 and the first housing 50 are not misaligned. Therefore, the drive shaft 20 can be rotated at a proper position, and the object in the biological lumen can be effectively cut and removed.

Second Embodiment

Figure 7:
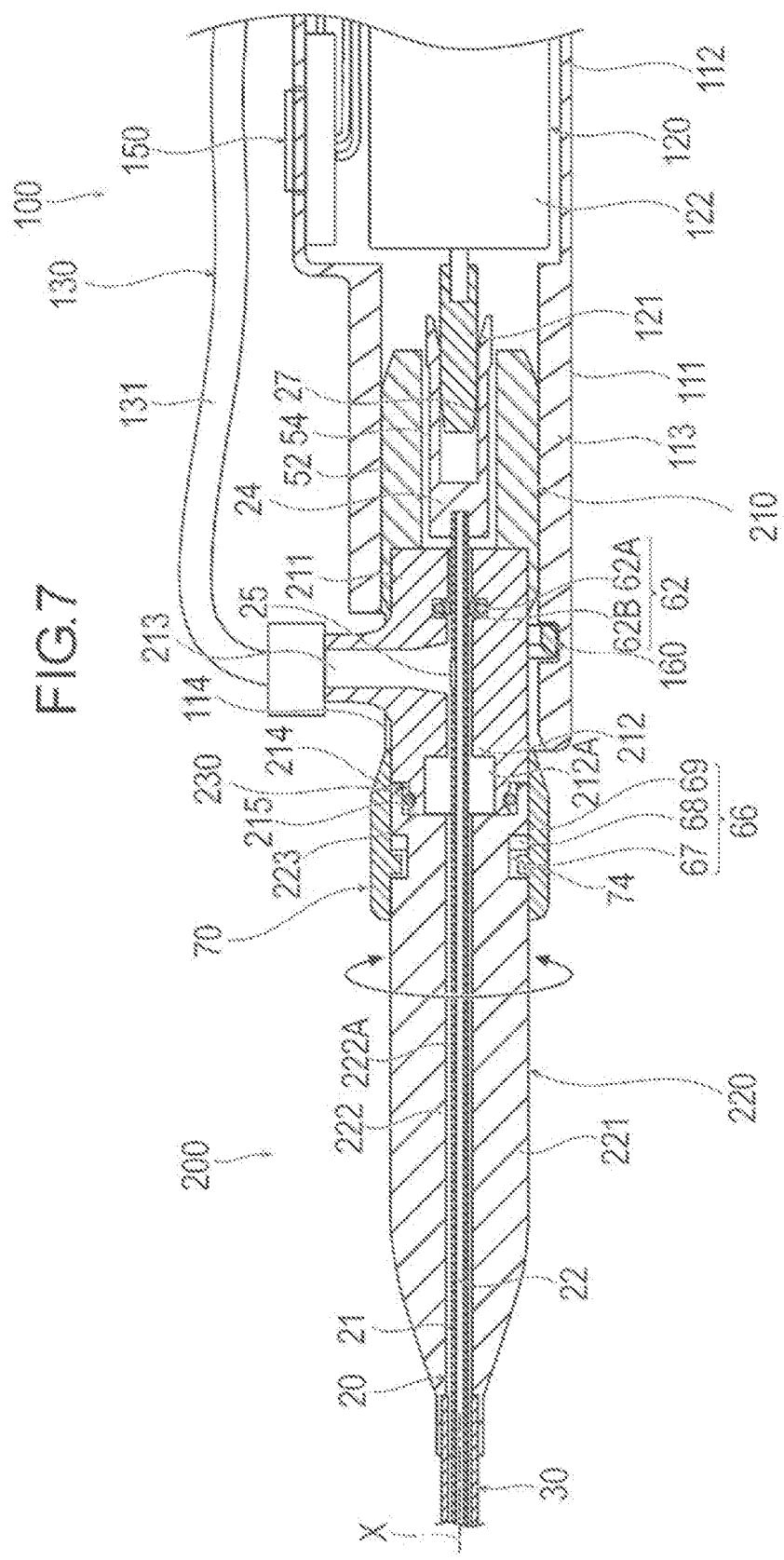
FIG. 7 is a sectional view illustrating a state before a projection portion is fitted into a recess portion in a medical device according to a second embodiment.

A medical device 200 according to a second embodiment is different from the medical device 10 according to the first embodiment in that an aspiration port 213 is disposed in a first housing 210 as illustrated in FIG. 7. The same reference numerals will be assigned to elements having the same functions as those according to the first embodiment, and description thereof will be omitted.

The first housing 210 includes a first housing main body 211 and the joint 52. The first housing main body 211 includes a first space-defining portion 212, the aspiration port 213, the first seal portion 62, and a sealing outer peripheral surface 214. The first space-defining portion 212 has a first internal space 212A through which the drive tube 21 rotatably penetrates. The aspiration tube 131 of the drive device 100 can be connected to the aspiration port 213. The aspiration port 213 communicates with the first internal space 212A. The proximal portion of the drive tube 21 that penetrates the outer tube 30 and a second housing 220 is located in the first internal space 212A. The outlet portion 25 of the drive tube 21 is located in the first internal space 212A. Therefore, the negative pressure acting on the aspiration port 213 from the aspiration tube 131 acts on the inside of the drive tube 21 from the outlet portion 25. The first seal portion 62 which comes into contact with the outer peripheral surface of the drive tube 21 is disposed on a proximal side of the first space-defining portion 212. The first seal portion 62 prevents the negative pressure in the first internal space 212A from being released.

The sealing outer peripheral surface 214 is disposed in a distal portion of the first housing main body 211. The sealing outer peripheral surface 214 is the outer peripheral surface located at a prescribed distance from the axis X of the drive tube 21. A cross-sectional shape of the sealing outer peripheral surface 214 is a smooth perfect circle. A sealing groove 215 in which a second seal portion 230 is disposed is formed on the sealing outer peripheral surface 214. The sealing groove 215 is formed to extend in the circumferential direction on the sealing outer peripheral surface 214. The sealing outer peripheral surface 214 is located apart from the support portion 70 inside the support portion 70 fixed to an outer peripheral surface of the distal portion of the first housing main body 211.

The second housing 220 located on a distal side of the first housing main body 211 includes a second housing main body 221, the engagement portion 66 which engages with the support portion 70, and a sealing inner peripheral surface 223. The second housing main body 221 includes a second space-defining portion 222. The second space-defining portion 222 has a second internal space 222A through which the drive tube 21 rotatably penetrates. The proximal end of the outer tube 30 is fixed to a distal portion of the second housing main body 221 in a liquid-tight manner.

The sealing inner peripheral surface 223 is disposed in a proximal portion of the second housing main body 221. The sealing inner peripheral surface 223 is the inner peripheral surface located at a prescribed distance from the axis X of the drive tube 21. A cross-sectional shape of the sealing inner peripheral surface 223 is a smooth perfect circle. The sealing inner peripheral surface 223 faces the sealing outer peripheral surface 214 of the first housing 210. The second seal portion 230 held by the sealing groove 215 of the sealing outer peripheral surface 214 is slidably in contact with the sealing inner peripheral surface 223. The sealing inner peripheral surface 223 and the sealing outer peripheral surface 214 are relatively rotatable. Furthermore, the sealing inner peripheral surface 223 and the sealing outer peripheral surface 214 are relatively movable along the axis X of the drive tube 21 while maintaining a predetermined separated distance. The sealing inner peripheral surface 223, the second seal portion 230, and the sealing outer peripheral surface 214 are surrounded by the support portion 70.

The relative movement of the first housing 210 and the second housing 220 is mainly manually performed. Therefore, the sealing inner peripheral surface 223 and the sealing outer peripheral surface 214 which pinch the second seal portion 230 are not moved at a relatively high speed. Therefore, unlike the first seal portion 62 which comes into contact with the drive tube 21, the second seal portion 230 does not need to have excellent slidability, wear resistance, and heat resistance. Therefore, the second seal portion 230 can adopt a material by giving priority to sealing performance. For example, the second seal portion 230 is an O-ring. For example, a configuration material of the second seal portion 230 includes natural rubber, synthetic rubber, and silicone resin.

In the drive device 100, the interlock port 111 has an accommodation portion 114 for receiving the aspiration port 213 disposed in the first housing 210.

Next, a method of using the medical device 200 according to the second embodiment will be described.

As in the medical device 10 according to the first embodiment, the medical device 200 can be interlocked by inserting the joint 52 of the first housing 210 into the receiving portion 113 of the drive device 100. At this time, the accommodation portion 114 is formed in the interlock port 111. Accordingly, the aspiration port 213 disposed in the first housing 210 can be disposed in the accommodation portion 114.

In the medical device 200 according to the second embodiment, the aspiration port 213 is disposed in the first housing 210. Therefore, the medical device 200 includes the first seal portion 62 disposed in a proximal portion of the first housing 210, and the second seal portion 230 disposed between the first housing 210 and the second housing 220. The second seal portion 230 for sealing the first internal space 212A is not disposed between the first housing main body 211 and the drive tube 21, but is disposed between the first housing 210 and the second housing 220. Therefore, the second seal portion 230 does not contact with the drive shaft 20 that rotates at a high speed because an inner diameter of the second seal portion 230 is larger than the drive tube 21. Therefore, it is possible to prevent damage to the second seal portion 230 by minimizing a load of the second seal portion 230. In addition, if the aspiration port 213 is disposed in the second housing 220, when the second housing 220 is rotated with respect to the first housing 210, the aspiration tube 131 may hinder the operation. In contrast, according to the present embodiment, the aspiration tube 131 is disposed in the first housing 210. Accordingly, it is easy to perform the operation for rotating the second housing 220 with respect to the first housing 210.

When rotating the outer tube 30, as illustrated in FIG. 7, the operator moves the second housing 220 to the proximal side with respect to the drive device 100 to which the first housing 210 is fixed. In this manner, the projection portion 74 of the support portion 70 is not fitted into the recess portion 68, and is movable in the circumferential direction along the groove portion 67. Therefore, the operator can rotate the second housing 220 with respect to the drive device 100 and the first housing 210. When the second housing 220 is rotated, the outer tube 30 fixed to the second housing 220 is rotated. When the second housing 220 is rotated with respect to the first housing 210, the sealing inner peripheral surface 223 and the sealing outer peripheral surface 214 are relatively rotated. At this time, sealing between the sealing inner peripheral surface 223 and the sealing outer peripheral surface 214 which are relatively rotated is maintained by the second seal portion 230.

After the operator adjusts the direction of the outer tube 30, as illustrated in FIG. 8, the operator moves the second housing 220 to the distal side with respect to the drive device 100 to which the first housing 210 is fixed. In this manner, the projection portion 74 of the support portion 70 is fitted into the recess portion 68 located in the second housing main body 221. Therefore, the second housing 220 cannot be rotated with respect to the first housing 210 and the drive device 100. That is, the second housing 220 can be integrally operated with the first housing 210 and the drive device 100.

When the second housing 220 is moved to a distal side with respect to the first housing 210, the sealing inner peripheral surface 223 moves to a distal side with respect to the sealing outer peripheral surface 214. At this time, sealing between the sealing inner peripheral surface 223 and the sealing outer peripheral surface 214 which are relatively moved is maintained by the second seal portion 230.

Next, the operator presses the switch 150. In this manner, the drive shaft 20 is rotated, and the pump 132 is operated. When the drive shaft 20 is rotated, the cutting portion 40 is rotated. The rotating cutting portion 40 cuts the thrombus inside the blood vessel.

When the pump 132 is operated, the negative pressure acts on the first internal space 212A via the aspiration tube 131. Therefore, the negative pressure acts on the aspiration lumen 22 of the drive tube 21 from the outlet portion 25 located in the first internal space 212A. Therefore, the thrombus cut by the blade 41 (refer to FIG. 3) of the cutting portion 40 passes through the inside of the cutting portion 40, and is aspirated into the aspiration lumen 22 from the inlet portion 26 of the drive tube 21. A proximal side of the first internal space 212A is sealed by the first seal portion 62, and a distal side thereof is sealed by the second seal portion 230. Therefore, the pressure loss of the first internal space 212A is extremely small. Therefore, the thrombus can be satisfactorily aspirated from the inlet portion 26.

As described above, in the medical device 200 according to the second embodiment, the first housing 210 has the aspiration port 213 that receives an aspiration force from the outside, and at least a portion of the drive shaft 20 has a tubular shape. The aspiration lumen 22 of the drive shaft 20 communicates with the aspiration port 213, one of the first housing 210 and the second housing 220 has the sealing inner peripheral surface 223, and the other has the sealing outer peripheral surface 214 which faces the sealing inner peripheral surface 223. The sealing inner peripheral surface 223 and the sealing outer peripheral surface 214 are rotatable relative to each other, and are relatively movable along the axis X of the drive shaft 20 while maintaining a predetermined separated distance. The ring-shaped second seal portion 230 is disposed between the sealing inner peripheral surface 223 and the sealing outer peripheral surface 214. In this manner, the medical device 200 can reduce the pressure loss due to the gap between the first housing 210 and the second housing 220, which are relatively rotatable and movable, by the second seal portion 230. Therefore, the medical device 200 can increase the aspiration force. The second seal portion 230 does not come into contact with the drive shaft 20 rotating at a high speed, and thus a material having a high sealing performance can be applied. In addition, since the relative movement and the relative inclination of the first housing 210 and the second housing 220 in the direction intersecting with the axis X are restricted, the load of the drive shaft 20 can be reduced.

Third Embodiment

Figure 10:
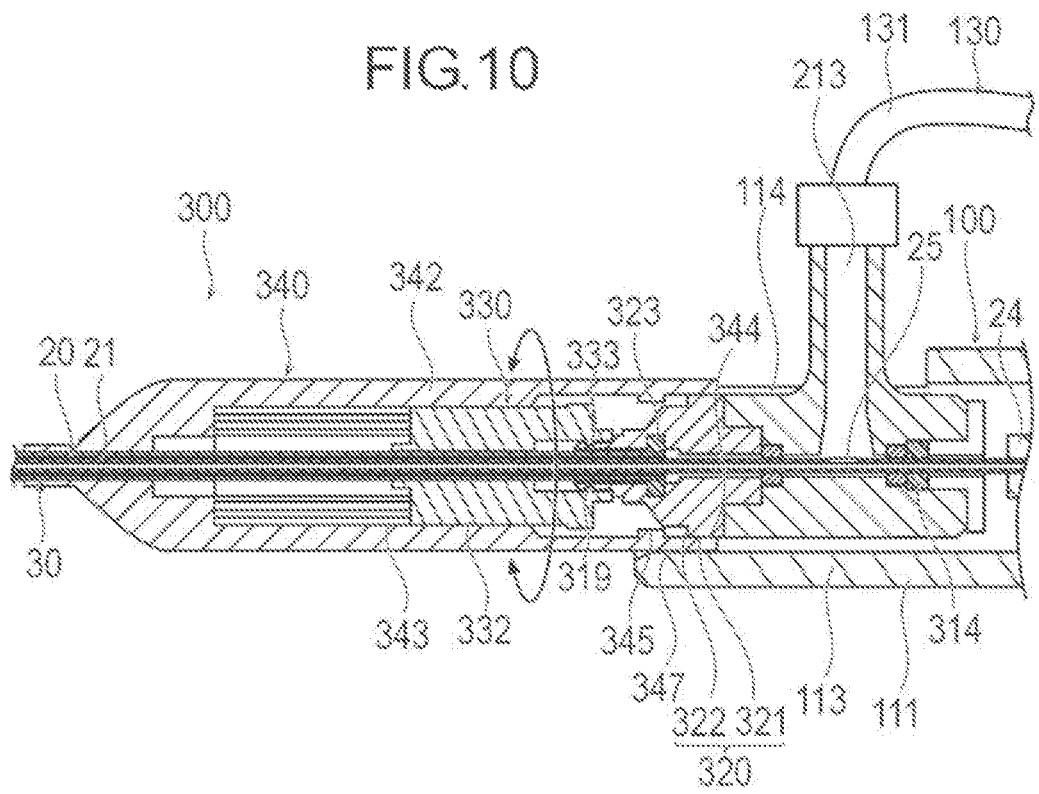
FIG. 10 is a sectional view illustrating a state before a projection portion is fitted into a recess portion in the medical device according to the third embodiment.

A medical device 300 according to a third embodiment is different from the medical device according to the first and second embodiments in that a support portion 340 can cover a second housing 330 as illustrated in FIG. 10. The same reference numerals will be assigned to elements having the same functions as those according to the first and second embodiments, and description thereof will be omitted.

Figures 9A, 9B:
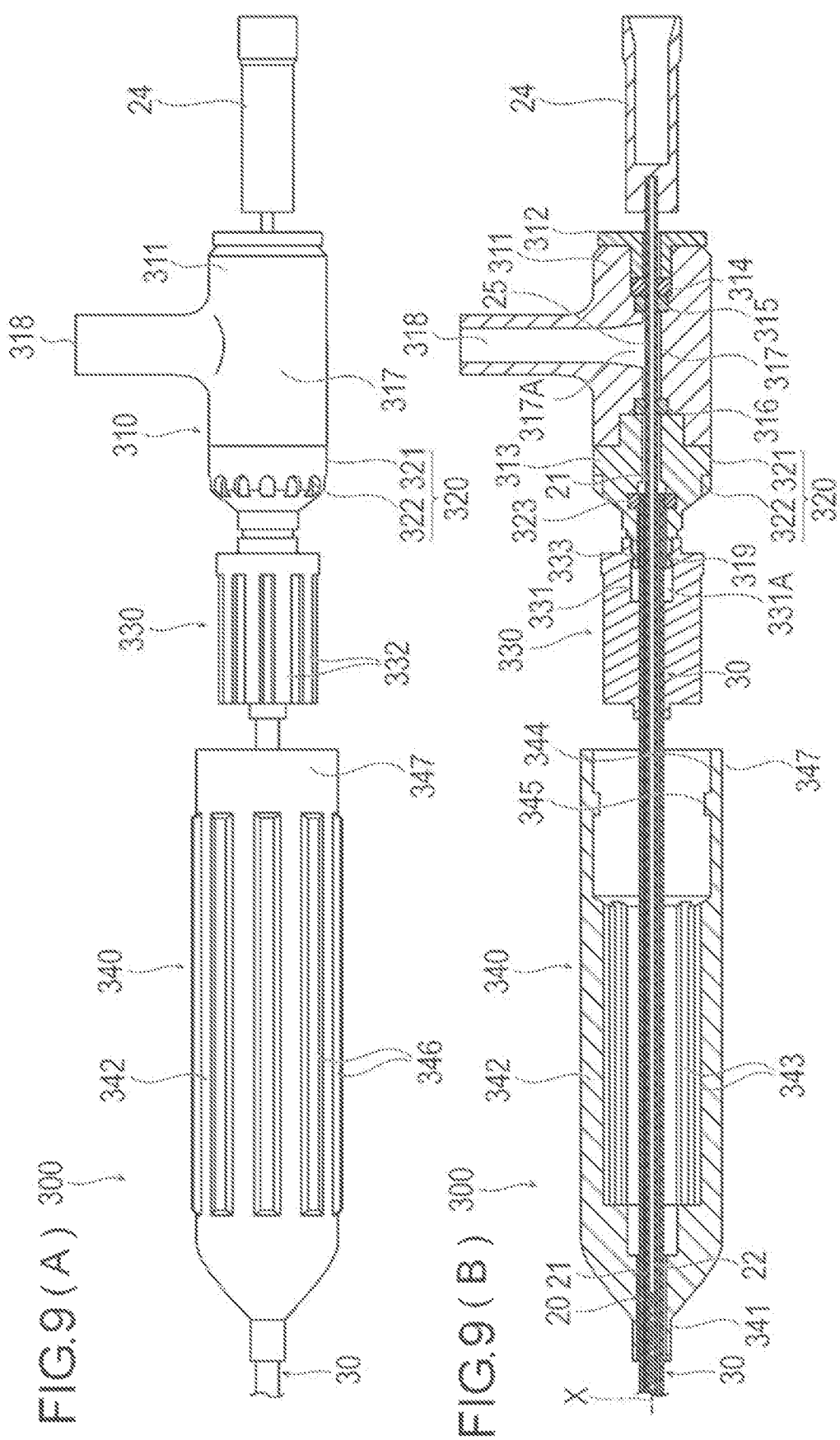
FIGS. 9A and 9B are views illustrating a proximal portion of a medical device according to a third embodiment.

As illustrated in FIGS. 9A and 9B, the medical device 300 according to the third embodiment includes a first housing 310 that holds the proximal portion of the drive shaft 20 to be rotatable, the second housing 330 fixed to the proximal portion of the outer tube 30, and the support portion 340.

The first housing 310 includes a first housing main body 311, a fixing member 312, an intermediate member 313, a first seal portion 314, a first bearing 315, a second bearing 316, and a third seal portion 323.

The first housing main body 311 includes a first space-defining portion 317 and an aspiration port 318. The first space-defining portion 317 has a first internal space 317A through which the drive tube 21 rotatably penetrates. The aspiration port 318 can connect the aspiration tube 131 of the drive device 100. The aspiration port 318 communicates with the first internal space 317A. The proximal portion of the drive tube 21 that penetrates the outer tube 30 and the second housing 330 is located in the first internal space 317A. The outlet portion 25 of the drive tube 21 is located in the first internal space 317A. Therefore, the negative pressure acting on the aspiration port 318 from the aspiration tube 131 acts on the inside of the drive tube 21 from the outlet portion 25. The first bearing 315 and the first seal portion 314 which are in contact with the outer peripheral surface of the drive tube 21 are disposed on a proximal side of the first space-defining portion 317. The first seal portion 314 prevents the negative pressure in the first internal space 317A from being released. The second bearing 316 which is in contact with the outer peripheral surface of the drive tube 21 is disposed on a distal side of the first space-defining portion 317. The first bearing 315 and the second bearing 316 hold the drive tube 21 to be smoothly rotatable around the axis X.

The fixing member 312 is fixed to a proximal side of the first housing main body 311. The fixing member 312 enters the first internal space 317A from the proximal side of the first housing main body 311. The fixing member 312 is in contact with the first seal portion 314, and fixes the first seal portion 314 and the first bearing 315. The drive tube 21 rotatably penetrates the fixing member 312.

The intermediate member 313 is fixed to a distal side of the first housing main body 311. The intermediate member 313 enters the first internal space 317A from the distal side of the first housing main body 311. The intermediate member 313 is contacted to the second bearing 316. The first seal portion 314 may be configured to include two seal portions, that is, the outer seal portion 62A and the inner seal portion 62B as in the first embodiment. The drive tube 21 rotatably penetrates the intermediate member 313. In addition, the intermediate member 313 internally has the third seal portion 323 that comes into contact with an outer peripheral surface of the outer tube 30. The third seal portion 323 prevents the negative pressure inside the first space-defining portion 317 from being released outward. The third seal portion 323 may be disposed in the second housing 330 instead of the first housing 310.

An interlock groove 319 rotatably interlocked with the second housing 330 and an engagement portion 320 engaging with the support portion 340 are disposed on an outer peripheral surface of the intermediate member 313. The interlock groove 319 extends in the circumferential direction. The engagement portion 320 has a sliding surface 321 which is a perfect circle having a smooth cross-sectional shape, and a plurality of recess portions 322 aligned in the circumferential direction. The sliding surface 321 may be disposed up to an outer peripheral surface of the first housing main body 311.

The second housing 330 is located on a distal side of the first housing 310. The second housing 330 is rotatably interlocked with the first housing 310. The second housing 330 may be movable in an axial direction with respect to the first housing 310 without being interlocked with the first housing 310. The second housing 330 includes a second space-defining portion 331 and an outer projection portion 332. The proximal portion of the outer tube 30 is fixed to the second housing 330. The second space-defining portion 331 has a second internal space 331A through which the drive tube 21 rotatably penetrates. The intermediate member 313 enters the second internal space 331A from a proximal side. An inner peripheral surface of the second space-defining portion 331 has an interlock projection portion 333 that is slidably fitted into the interlock groove 319 of the intermediate member 313. The interlock projection portion 333 is fitted into the interlock groove 319. In this manner, the second housing 330 is rotatably interlocked with the first housing 310. The outer projection portion 332 extends toward a proximal side from a distal end of an outer peripheral surface of the second housing 330.

The support portion 340 is a tubular member that guides and limits the relative rotation of the first housing 310 and the second housing 330. The support portion 340 includes a sliding hole 341 through which the outer tube 30 slidably penetrates, and a cover portion 342 that can accommodate the second housing 330. The sliding hole 341 is located on a distal side of the support portion 340. The support portion 340 is movable to a distal side and a proximal side along the outer tube 30 that penetrates the sliding hole 341. The cover portion 342 is open on a proximal side so that the whole second housing 330 and a distal portion of the first housing 310 can be covered.

On an inner peripheral surface of the cover portion 342, a plurality of inner recess portions 343 which can be fitted to the outer projection portions 332 of the second housing 330 are aligned at an equal interval in the circumferential direction. Each of the inner recess portions 343 extends along the axis X. In addition, on the inner peripheral surface of the cover portion 342, a proximal side of the inner recess portion 343 has a support sliding surface 344 which is a perfect circle having a smooth cross-sectional shape, and a plurality of projection portions 345 aligned in the circumferential direction. An inner diameter of the support sliding surface 344 is slightly larger than an outer diameter of the sliding surface 321 of the second housing 330. The support sliding surface 344 slidably comes into close contact with the sliding surface 321. The projection portion 345 has a shape projecting to a proximal side while projecting inward in the radial direction from the support sliding surface 344. It is preferable that the number of the projection portions 345 coincides with the number of the recess portions 322, but the numbers may not coincide with each other. The projection portion 345 has a shape that can be fitted into the recess portion 322 toward the proximal side and can be detached from the recess portion 322 toward the distal side. The projection portion 345 can be fitted into any of the recess portions 322 of the second housing 330. An outer peripheral surface of the support portion 340 has a plurality of friction portions 346 and a support interlock portion 347. The friction portion 346 projects to increase friction so that the operator can easily operate the friction portion 346 with the hand. The support interlock portion 347 is located in a proximal portion of the outer peripheral surface of the support portion 340. The support interlock portion 347 can be slidably interlocked with the receiving portion 113 of the drive device 100.

Next, a method of using the medical device 300 according to the third embodiment will be described.

As illustrated in FIG. 10, the operator can move the support portion 340 to a proximal side with respect to the second housing 330, and can cover the second housing 330 and the first housing 310 with the cover portion 342. In this manner, the outer projection portion 332 of the second housing 330 is fitted into the inner recess portion 343 of an inner peripheral surface of the support portion 340. In this manner, the second housing 330 cannot be rotated with respect to the support portion 340. When the support portion 340 is rotated in a state where the projection portion 345 of the support portion 340 is not fitted into the recess portion 322 of the first housing 310, the second housing 330 is also rotated together. An outer diameter of the support portion 340 is larger than an outer diameter of the second housing 330. Accordingly, the operator can easily rotate the support portion 340. In addition, the friction portion 346 (refer to FIGS. 9A and 9B) that increases the friction is formed on the outer peripheral surface of the support portion 340. Accordingly, the operator can easily rotate the support portion 340 by using the friction portion 346. Therefore, the operator can easily rotate the second housing 330 and the outer tube 30 fixed to the second housing 330 by rotating the support portion 340. In this manner, the direction of the curved portion 34 of the outer tube 30 is changed. Therefore, the position of the cutting portion 40 can be changed without rotating the drive device 100 (refer to FIG. 1).

In addition, when the support portion 340 covers the second housing 330, the support sliding surface 344 of the support portion 340 slidably comes into contact with the sliding surface 321 of the first housing 310. In this manner, the axes of the first housing 310, the second housing 330, and the support portion 340 coincide with each other without misalignment. In addition, the support portion 340 restricts the relative inclination of the first housing 310 and the second housing 330. Therefore, even when the first housing 310 and the second housing 330 are relatively rotated, the drive shaft 20 can be rotated at a proper position. Therefore, in the medical device 300, the cutting portion 40 fixed to the drive shaft 20 can effectively cut and remove the object in the biological lumen. In addition, even if the second housing 330 has a structure which can be separated from the first housing 310 in the axial direction, the support portion 340 can restrict the relative movement and the relative inclination of the first housing 310 and the second housing 330 in the direction intersecting with the axis X. Therefore, the load of the drive shaft 20 can be reduced.

In addition, the support interlock portion 347 of the support portion 340 slidably comes into contact with the receiving portion 113 of the interlock port 111. In this manner, the support portion 340 prevents the axes of the first housing 310 and the second housing 330 from being misaligned with the axis of the drive device 100. Therefore, the drive shaft 20 can be rotated at a proper position.

Figure 11:
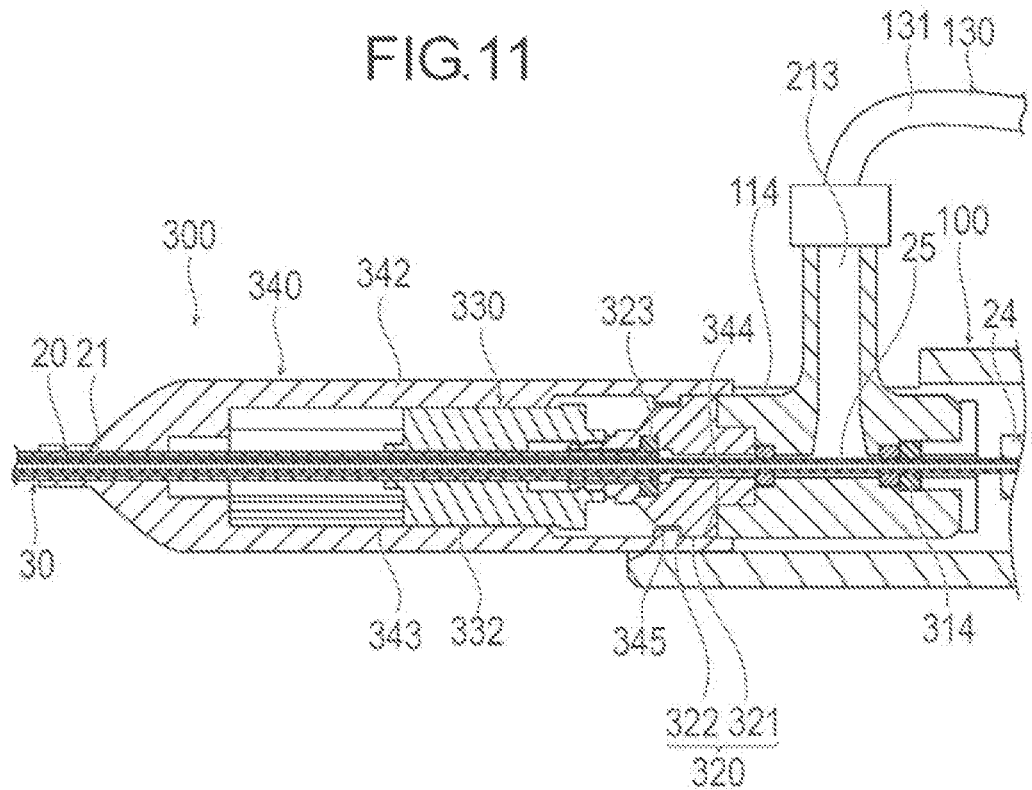
FIG. 11 is a sectional view illustrating a state where the projection portion is fitted into the recess portion in the medical device according to the third embodiment.

After adjusting the direction of the outer tube 30, the operator can further move the support portion 340 to the proximal side with respect to the second housing 330. In this manner, as illustrated in FIG. 11, the projection portion 345 of the support portion 340 is fitted into any one of the recess portions 322 of the first housing 310. In this manner, the support portion 340 cannot be rotated with respect to the first housing 310. Therefore, the first housing 310, the second housing 330, and the support portion 340 can be integrally operated, thereby improving operability.

In addition, the aspiration port 318 is disposed in the first housing 310 instead of the second housing 330. Therefore, when the support portion 340 and the second housing 330 are rotated, the aspiration port 318 is not rotated. Therefore, it is easy to perform the operation for rotating the support portion 340.

Next, the operator presses the switch 150 (refer to FIG. 1). In this manner, the drive shaft 20 is rotated, and the pump 132 is operated. When the drive shaft 20 is rotated, the cutting portion 40 is rotated. The rotating cutting portion 40 cuts the thrombus inside the blood vessel.

When the pump 132 is operated, the negative pressure acts on the first internal space 317A via the aspiration tube 131. Therefore, the negative pressure acts on the aspiration lumen 22 of the drive tube 21 from the outlet portion 25 located in the first internal space 317A. Therefore, the thrombus cut by the blade 41 of the cutting portion 40 is aspirated into the aspiration lumen 22. A proximal side of the first internal space 317A is sealed by the first seal portion 314, and a distal side thereof is sealed by the third seal portion 323. Therefore, the pressure loss of the first internal space 317A is extremely small. Therefore, the thrombus can be satisfactorily aspirated from the inlet portion 26.

As described above, in the medical device 300 according to the third embodiment, the first housing 310 has the aspiration port 318 that receives the aspiration force from the outside. The support portion 340 has the cover portion 342 that covers the second housing 330. The second housing 330 is covered with the cover portion 342 to be rotatable with the support portion 340. In this manner, the second housing 330 can be rotated by the support portion 340 having the outer diameter larger than that of the second housing 330. Therefore, the operator can easily rotate the second housing 330 and the outer tube 30 via the support portion 340.

In addition, an outer peripheral surface of the cover portion 342 has the support interlock portion 347 interlocked with the drive device 100 that transmits the drive force to the drive shaft 20. In this manner, the support portion 340 may be interlocked with the drive device 100 while internally accommodating and supporting the second housing 330. The support portion 340 is located between the second housing 330 and the drive device 100. Therefore, the support portion 340 can effectively restrict the relative movement and the relative inclination of the drive device 100, the first housing 310, and the second housing 330 in the direction intersecting with the axis X.

The present invention is not limited to the above-described embodiments, and various modifications can be made by those skilled in the art within the technical idea of the present invention. For example, the biological lumen into which the medical device is inserted is not limited to the blood vessel, and may be a vessel, a ureter, a bile duct, a fallopian tube, or a hepatic duct, for example. Therefore, an object to be destroyed may not be the thrombus.

In addition, the support portion may be a portion of the configuration of the first housing or the second housing. Therefore, the support portion may be integrally formed with the first housing or the second housing.

In addition, in the above-described first and second embodiments, the second housing is moved to the distal side with respect to the first housing. In this manner, the projection portion is fitted into the recess portion, and the second housing is rotatable integrally with the first housing. However, the configuration may be reversed. That is, the second housing may be moved to the proximal side with respect to the first housing. In this manner, the projection portion may be fitted into the recess portion, and the second housing may be rotatable integrally with the first housing.

In addition, in the medical device 200 according to the second embodiment, the sealing inner peripheral surface 223 is disposed in the second housing 220, and the sealing outer peripheral surface 214 is disposed in the first housing 210. However, the sealing inner peripheral surface may be disposed in the first housing, and the sealing outer peripheral surface may be disposed in the second housing. In addition, the sealing groove for holding the second seal portion may be disposed on the sealing inner peripheral surface instead of the sealing outer peripheral surface.

In addition, the medical device and the drive device may be integrally configured. In addition, the outlet portion of the drive shaft may be formed in the proximal end instead of the side surface of the drive shaft. In this case, a drive source (motor) of the drive shaft may be located on the side surface side instead of the proximal side of the drive shaft. For example, the drive shaft can receive the rotational drive force from the side surface side via a gear by installing the gear on the outer peripheral surface.

In addition, in the third embodiment illustrated in FIGS. 9A and 9B, the first housing 310 and the second housing 330 may come into slidable contact with each other so that the relative rotation is restricted. For example, an outer diameter of the interlock projection portion 333 may substantially coincide with an inner diameter of the interlock groove 319, and the interlock projection portion 333 may be press-fitted into the interlock groove 319. In this manner, the first housing 310 and the second housing 330 come into contact with each other with resistance that does not allow the relative rotation unless the operator applies a certain degree of the rotational force. Therefore, in the medical device 300, the first housing 310 and the second housing 330 can be aligned at any desired position in the circumferential direction without moving the support portion 340 to the proximal side and fitting the projection portion 345 into the recess portion 322. Therefore, without moving the support portion 340 in the axial direction, the position of the cutting portion 40 can be easily changed in any desired direction by integrally or separately rotating the first housing 310 and the second housing 330.

In addition, the second housing 330 is disposed at a fixed position in the axial direction of the drive shaft 20 with respect to the first housing 310. That is, the second housing 330 does not move in the axial direction with respect to the first housing 310. Therefore, the first housing 310 and the second housing 330 can be integrally or separately rotated without moving the second housing 330 in the axial direction with respect to the first housing 310. Therefore, the position of the cutting portion 40 can be easily changed in any desired direction. In addition, the relative movement and the relative inclination of the first housing 310 and the second housing 330 in the direction intersecting with the axis X are restricted. Accordingly, the load of the drive shaft 20 can be reduced.

In addition, as a modification example of the third embodiment, for example, the interlock projection portion 333 may be a deformable valve body, and may be disposed in the interlock groove 319 in a compressed state. In this manner, the interlock projection portion 333 and the interlock groove 319 can come into contact with each other with resistance that does not allow the relative rotation unless the operator applies a certain degree of the rotational force. A position for disposing the valve body is not particularly limited as long as the first housing 310 and the second housing 330 slide together at the position. Therefore, the valve body that restricts the rotation of the first housing 50 and the second housing 60 may be disposed at a position different from that of the interlock projection portion 333 of the second housing 330 or in the first housing 310.

In addition, the first housing 310 and the support portion 340 may come into slidable contact with each other to restrict the relative rotation. For example, in the third embodiment illustrated in FIG. 10, the sliding surface 321 of the first housing 310 and the support sliding surface 344 of the support portion 340 may come into slidable contact with each other to restrict the relative rotation. At this time, the projection portion 345 of the support portion 340 is not fitted into the recess portion 322 of the first housing 310. The support portion 340 is interlocked with the second housing 330, and can be rotated together with the second housing 330. In this manner, the relative rotation of the first housing 310 and the support portion 340 is restricted. Accordingly, the relative rotation of the first housing 310 and the second housing 330 is restricted. Therefore, in the medical device 300, the first housing 310 and the second housing 330 can be aligned at any desired position in the circumferential direction without moving the support portion 340 to the proximal side and fitting the projection portion 345 into the recess portion 322. Therefore, the position of the cutting portion 40 can be easily changed in any desired direction by integrally or separately rotating the first housing 310 and the second housing 330. As described above, if the first housing 310 and the second housing 330 can be aligned at any desired position in the circumferential direction without fitting the projection portion 345 into the recess portion 322, the projection portion 345 and the recess portion 322 may not be provided as in the modification example of the third embodiment illustrated in FIGS. 12A and 12B.

The detailed description above describes embodiments of a medical device and method for removing an object in a biological lumen representing examples of the medical device and method disclosed here. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A medical device for removing an object inside a biological lumen, comprising:
   a drive shaft that is rotatable about a rotation axis;
   a cutting portion fixed to a distal portion of the drive shaft and configured to cut the object;
   a first housing that accommodates the drive shaft to be rotatable relative to the first housing;
   a second housing located on a distal side of the first housing and rotatable with respect to the first housing around the rotation axis, wherein the drive shaft is rotatable relative to the second housing; and
   a support portion that supports the first housing and the second housing, wherein the drive shaft is rotatable relative to the support portion,
   wherein one of the first housing, the second housing, and the support portion has a recess portion, and an other one of the first housing, the second housing, and the support portion has a projection portion fittable into and detachable from the recess portion by relatively moving along the rotation axis,
   wherein the projection portion and the recess portion are configured to be fitted together to restrict relative rotation of the first housing and the second housing,
   wherein the support portion supports at least one of the first housing and the second housing to be rotatable around the rotation axis.

2. The medical device according to claim 1,
   wherein a first seal portion which comes into contact with an outer peripheral surface of the drive shaft is disposed in a proximal portion of the first housing or the second housing in which an aspiration port is formed.

3. The medical device according to claim 2,
   wherein the first seal portion has
      a ring-shaped outer seal portion which comes into contact with the first housing or the second housing; and
      a ring-shaped inner seal portion which comes into contact with the drive shaft,
   wherein the outer seal portion is more flexible than the inner seal portion, and
   wherein the inner seal portion comes into contact with an inner peripheral surface of the outer seal portion, and the inner seal portion has frictional resistance smaller than that of the outer seal portion.

4. The medical device according to claim 1, further comprising:
   an outer tube fixed to the second housing and accommodating the drive shaft to be rotatable relative to the outer tube.

5. The medical device according to claim 1,
   wherein the second housing is movable with respect to the first housing along the rotation axis.

* * * * *